United States Patent [19]

Nefedov et al.

[11] Patent Number: 6,008,407
[45] Date of Patent: Dec. 28, 1999

[54] METHOD OF PREPARING FLUOROAROMATIC COMPOUNDS

[75] Inventors: Oleg Matveyevich Nefedov; Nikolay Vasiljcvich Volchkov; Mariya Borisovna Lipkind, all of Moscow, Russian Federation; Ho Seong Lee, Taejeon, Rep. of Korea; Young Jun Park, Taejeon, Rep. of Korea; Min Hwan Kim, Taejeon, Rep. of Korea

[73] Assignees: Zelinsky Institute of Organic Chemistry, Moscow, Russian Federation; Samsung General Chemicals Co., Ltd., Chungnam, Rep. of Korea

[21] Appl. No.: 09/185,171

[22] Filed: Nov. 3, 1998

[51] Int. Cl.[6] .......................... C07C 51/58; C07C 51/16; C07C 25/13
[52] U.S. Cl. .......................... 562/422; 562/859; 570/143; 570/144; 570/146
[58] Field of Search .................................. 562/422, 859; 570/143, 144, 146

[56] References Cited

U.S. PATENT DOCUMENTS

| 3,499,942 | 3/1970 | Nefedov et al. . | |
|---|---|---|---|
| 4,374,266 | 2/1983 | Fifolt et al. . | |
| 4,754,084 | 6/1988 | Weigert . | |
| 4,968,830 | 11/1990 | Tang | 570/146 |
| 5,003,103 | 3/1991 | Fertel et al. . | |

FOREIGN PATENT DOCUMENTS

| 2019540 | 1/1987 | Japan | 570/146 |
|---|---|---|---|
| 0 431 373 A2 | 11/1990 | WIPO . | |

*Primary Examiner*—Alan Siegel
*Attorney, Agent, or Firm*—Law Offices of Jane Massey Licata

[57] ABSTRACT

The present invention provides a method of preparing ortho-difluorobenzene derivatives, which comprises (a) providing a mixture of cyclohexenes by reacting chlorotrifluoroethylene (CTFE) and 1.3-diene in a flow reactor and distilling the resultant, and (b) dehydrohalogenating the mixture of cyclohexenes with a phase transition catalyst in :he presence of alkali metal hydroxide at temperature range of 40 to 150° C. without using any organic solvent. The distillate having low boiling point, which is obtained during distillation of the resultant, is recycled into the flow reactor. The present invention also provides a method of preparing 2-chloro-4,5-difluorobenzoic acid, which comprises (a) providing a mixture of 4-chloro-1-methyl-4,5,5-trifluorocyclohexene and 5-chloro-1-methyl-4,4,5-trifluorocyclohexene by reacting chlorotrifluoroethylene (CTFE) and isoprene and distilling the resultant. (b) dehydrohalogenating said mixture in the presence of alkali metal hydroxide and a phase transition catalyst to form 3,4-difluorotoluene, to reacting said 3,4-difluorotoluene with chlorine gas without using any organic solvent to form 2-chloro-4,5-difluorotoluene, (d) photo-reacting said 2-chloro-4,5-difluorotoluene with chlorine gas under a lighting mercury lamp without using any organic solvent to form 2-chloro-4,5-difluorobenzotrichloride, and (e) reacting said 2-chloro-4,5-difluorobenzotrichloride with aqueous acid solution without using any organic solvent. The present invention also provides a method of preparing 2-chloro-4,5-difluorobenzoyl chloride by reacting the 2-chloro-4,5-difluorobenzotrichloride of step (e) above with zinc oxide.

9 Claims, No Drawings

METHOD OF PREPARING FLUOROAROMATIC COMPOUNDS

FIELD OF THE INVENTION

The present invention relates to a method of preparing fluoroaromatic compounds, which shows high productivity, simple process and low cost of preparation. More particularly, the present invention relates to a method of preparing 2-chloro-4,5-difluorobenzoic acid and 2-chloro-4,5-difluorobenzoyl chloride via formation of ortho-difluorobenzene derivatives prepared by reacting chlorotrifluoroethylene with 1,3-diene.

BACKGROUND OF THE INVENTION

Conventional methods for synthesis of fluoroaromatic compounds are based on direct substitution of the hydrogen atoms or suitable functional groups of the aromatic ring with fluorine of a fluorinating agent. U.S. Pat. No. 3,499,942 discloses an alternative method of preparing aromatic compounds using a fluorosynthon.

2-chloro-4,5-difluorobenzoyl chloride which is normally prepared from 2-chloro-4,5-difluorobenzoic acid is used as a particularly valuable intermediate for synthesis of quinolone carboxylic acids which have a strong antibiotic activity.

U.S. Pat. No. 4,374,266 discloses fluorophthalamic acids and ammonium salts thereof, and a method for the preparation of these compounds. U.S. Pat. No. 5,003,103 discloses a preparation of 2-chloro-4,5-difluorobenzoic acid which is prepared by decarboxylating 4,5-difluorophthalic anhydride or 4,5-difluorophthalic acid to form 3,4-difluorobenzoic acid in N-methyl-2-pyrrolidone, quinoline, or dimethyl acetamide, treating the 3,4-difluorobenzoic acid with a mixture of nitric and sulfuric acids to produce 2-nitro-4,5-difluorobenzoic acid, and treating the 2-nitro-4,5-difluorobenzoic acid with elemental chlorine. European Patent Publication No. 431 373 A2 discloses a process for producing 5-fluorbenzoic acids which comprises trichloromethylating a fluorobenzene to obtain a 5-fluorobenzotrichloride, reacting with aqueous ammonia to obtain a 5-fluorobenzonitrile, reacting with a fluorinating agent to obtain a 5-fluorobenzonitrile, and hydrolyzing it. However, all of these methods have shortcomings of either longer reaction steps or using expensive reagents.

Generally, the 2-chloro-4,5-difluorobenzoyl chloride has been prepared by reacting 2-chloro-4,5-difluorobenzoic acid with thionyl chloride.

U.S. Pat. No. 4,754,084 discloses a preparation of substituted fluorobenzenes which is produced by pyrolyzing vinylfluorocyclobutanes in the presence of activated carbon or certain metal oxides or mixtures of metal oxides. In this invention, a tetrafluoroethylene was used to prepare the substituted fluorobenzenes, which tends to polymerize spontaneously in the presence of traces of oxygen. Therefore, the tetrafluoroethylene should be stored at low temperature without contacting air. In the pyrolysis of vinylfluorocyclobutane derivatives, it forms easily polymeric by-products which affects badly a yield of products and cause difficulties in mass production, thus it is always required to react in a nitrogen gas atmosphere.

In addition, the methods described above have a difficulty for isolation of the desired product because of formation of structurally similar by-products.

Accordingly, to overcome the shortcomings as described above, the present inventors have developed methods of preparing 2-chloro-4,5-difluorobenzoic acid and 2-chloro-4,5-difluorobenzoyl chloride without passing via vinylfluorocyclobutane derivatives.

OBJECTS OF THE INVENTION

An object of the present invention is to provide a method of preparing ortho-difluorobenzene derivatives having a high yield.

Another object of the invention is to provide methods of preparing 2-chloro-4,5-difluorobenzoic acid and 2-chloro-4,5-difluorobenzoyl chloride having a high productivity.

A further object of the invention is to provide methods of preparing 2-chloro-4,5-difluorobenzoic acid and 2-chloro-4,5-difluorobenzoyl chloride from ortho-difluorobenzene derivatives, which obviates a step of forming vinylfluorocyclobutane as an intermediate.

A further object of the invention is to provide methods of preparing 2-chloro-4,5-difluorobenzoic acid and 2-chloro-4,5-difluorobenzoyl chloride having a simple process and low cost of preparation thereof.

A further object of the invention is to provide methods of preparing 2-chloro-4,5-difluorobenzoic acid and 2-chloro-4,5-difluorobenzoyl chloride without using an organic solvent.

A further object of the invention is to provide methods of preparing 2-chloro-4,5-difluorobenzoyl chloride which obviates a step of forming 2-chloro-4,5-difluorobenzoic acid as an intermediate.

These and other objects and advantages may found in various embodiments of the present invention. It is not necessary that each and every object or advantage be found in all embodiments of the present invention. Other objects and advantages of this invention will be apparent from the ensuing disclosure and appended claims.

SUMMARY OF THE INVENTION

The present invention provides a method of preparing ortho-difluorobenzene derivatives, which comprises (a) providing a mixture of cyclohexenes by reacting chlorotrifluoroethylene (CTFE) and 1,3-diene in a flow reactor at temperature range of 390 to 480° C. under atmospheric pressure through continuous vapor phase condensation and distilling the resultant, and (b) dehydrohalogenating the mixture of cyclohexenes with a phase transition catalyst in the presence of alkali metal hydroxide at temperature range of 40 to 150° C. without using any organic solvent. In step (a), the molar ratio of chlorotrifluoroethylene (CTFE) to 1,3-diene is in the range of 1.5:1 to 0.8:1, and the reaction time is in the range of 0.2 to 30 sec. The distillate having low boiling point, which is obtained during distillation of the resultant, is recycled into the flow reactor.

The present invention also provides a method of preparing 2-chloro-4,5-difluorobenzoic acid, which comprises (a) providing a mixture of 4-chloro-1-methyl-4,5,5-trifluorocyclohexene and 5-chloro-1-methyl-4,4,5-trifluorocyclohexene by reacting chlorotrifluoroethylene (CTFE) and isoprene at temperature range of 390 to 480° C. through continuous vapor phase condensation in a flow reactor and distilling the resultant, (b) dehydrohalogenating said mixture in the presence of alkali metal hydroxide and a phase transition catalyst to form 3,4-difluorotoluene, (c) reacting said 3,4-difluorotoluene with chlorine gas in the presence of catalysts consisting of ferro-shaving and ferric chloride at temperature range of −10 to 40° C. without using any organic solvent to form 2-chloro-4,5-difluorotoluene, (d) photo-reacting said 2-chloro-4,5-difluorotoluene with chlorine gas under a lighting mercury lamp at temperature range of 80 to 140° C. without using any organic solvent to form 2-chloro-4,5-difluorobenzotrichloride, and (e) reacting said 2-chloro-4,5-difluorobenzotrichloride with aqueous acid solution at temperature range of 35 to 80° C. without using any organic solvent. The present invention also provides a method of preparing 2-chloro-4,5-difluorobenzoyl chloride by reacting the 2-chloro-4,5-difluorobenzotrichloride of step (e) above with zinc oxide.

DETAILED DESCRIPTION OF THE INVENTION

The present invention relates to methods of preparing 2-chloro-4,5-difluorobenzoic acid and 2-chloro-4,5-difluorobenzoyl chloride via formation of ortho-difluorobenzene derivatives that are prepared by reacting chlorotrifluoroethylene with 1,3-diene, which shows high productivity, simple process and low cost of preparation. The method of preparing ortho-difluorobenzene derivatives is represented by the following reaction:

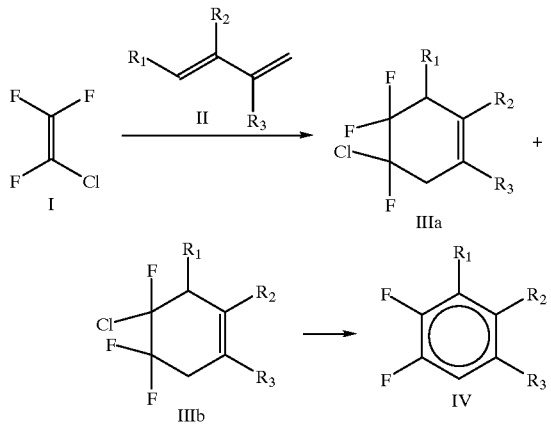

wherein $R_1$, $R_2$ and $R_3$ are independently a hydrogen atom or a lower alkyl group, preferably a methyl group.

The method of preparing ortho-difluorobenzene derivatives comprises (a) providing a mixture of cyclohexenes by reacting chlorotrifluoroethylene (CTFE) and 1,3-diene in a flow reactor at temperature range of 390 to 480° C. under atmospheric pressure through continuous vapor phase condensation and distilling the resultant, and (b) dehydrohalogenating the mixture of cyclohexenes with a phase transition catalyst in the presence of alkali metal hydroxide at temperature range of 40 to 150° C. without using any organic solvent.

In the first step (a) of the method, chlorotrifluoroethylene (CTFE) (I) and 1,3-diene (II) are continuously reacted at the vapor phase in a flow reactor to produce a mixture of cyclohexenes (IIIa) and (IIIb) through condensation and the mixture is distilled. In step (a), the molar ratio of chlorotrifluoroethylene (CTFE) to 1,3-diene is in the range of 1.5:1 to 0.8:1, and the reaction time is in the range of 0.2 to 30 sec, preferably 5 to 15 sec. The reaction temperature is in the range of 390 to 480° C., preferably 420 to 470° C. If the reaction temperature is higher than 480° C., the yield of the mixture of cyclohexenes (IIIa and IIIb) is remarkably decreased because of formation of undesired tars and polymers which give a potential hazard that a flow reactor may be clogged by the polymers. Also, by lowering the reaction temperature, a cost of energy can be reduced as well. The distillate having low boiling point is obtained during distillation of the resultant, and the distillate is recycled into the flow reactor.

The second step (b) of the method is elimination of halogenated atoms from the mixture of cyclohexenes (IIIa and IIIb). The mixture of cyclohexenes is dehydrohalogenated with a phase transition catalyst in the presence of alkali metal hydroxide at temperature range of 40 to 150° C. without using any organic solvent to prepare ortho-difluorobenzene derivatives (IV). In this invention, the alkali metal hydroxide is preferably potassium hydroxide or sodium hydroxide, and the phase transfer catalyst is preferably 18-crown-6, tetrabutylammonium bromide or benzyltriethylammonium chloride.

The method of preparing ortho-difluorobenzene derivatives according to the present invention has advantages of providing an energy-saving process by lowering the reaction temperature and of providing a high efficiency process by recycling the distillate having low boiling point which is produced during distillation of the mixture of cyclohexenes, which are superior to the conventional methods for preparation thereof. In addition, the method of the present invention is a simple process, therefore it is a very competitive method of preparing 2-chloro-4,5-difluorobenzoic acid and 2-chloro-4,5-difluorobenzoyl chloride from ortho-difluorobenzene derivatives, which obviates a step of forming vinylfluorocyclobutane as an intermediate.

The ortho-difluorobenzene derivatives prepared in the above reaction is employed to prepare 2-chloro-4,5-difluorobenzoic acid and 2-chloro-4,5-difluorobenzoyl chloride.

The method of preparing 2-chloro-4,5-difluorobenzoic acid and 2-chloro-4,5-difluorobenzoyl chloride in accordance with the present invention is represented as follow:

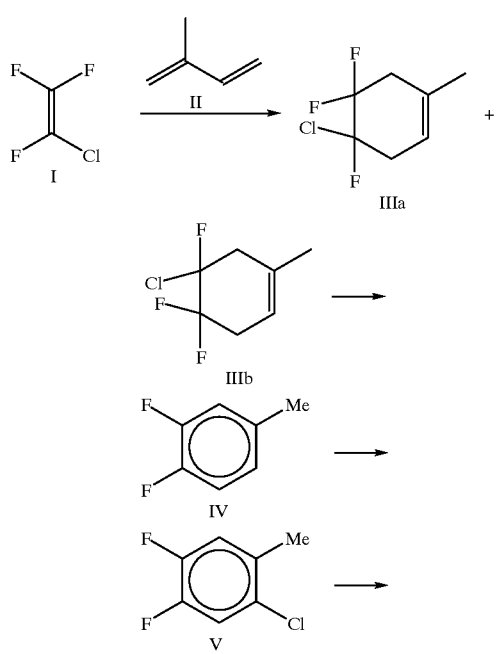

-continued

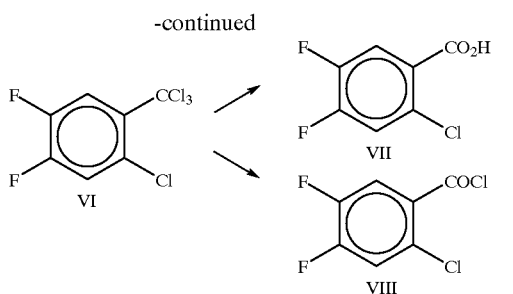

wherein Me represents a methyl group.

The present invention also provides a method of preparing 2-chloro-4,5-difluorobenzoic acid, which comprises (a) providing a mixture of 4-chloro-1-methyl-4,5,5-trifluorocyclohexene and 5-chloro-1-methyl-4,4,5-trifluorocyclohexene by reacting chlorotrifluoroethylene (CTFE) and isoprene at temperature range of 390 to 480° C. through continuous vapor phase condensation in a flow reactor and distilling the resultant, (b) dehydrohalogenating said mixture in the presence of alkali metal hydroxide and a phase transition catalyst to form 3,4-difluorotoluene, (c) reacting said 3,4-difluorotoluene with chlorine gas in the presence of catalysts consisting of ferro-shaving and ferric chloride at temperature range of −10 to 40° C. without using an organic solvent to form 2-chloro-4,5-difluorotoluene, (d) photo-reacting said 2-chloro-4,5-difluorotoluene with chlorine gas under a lighting mercury lamp at temperature range of 80 to 140° C. without using any organic solvent to form 2-chloro-4,5-difluorobenzotrichloride, and (e) reacting said 2-chloro-4,5-difluorobenzotrichloride with aqueous acid solution at temperature range of 35 to 80° C. without using any organic solvent.

As shown in the above reaction, a mixture of 4-chloro-1-methyl-4,5,5-trifluorocyclohexene (IIIa) and 5-chloro-1-methyl-4,4,5-trifluorocyclohexene (IIIb) is prepared by reacting chlorotrifluoroethylene (CTFE) (I) and isoprene (II) at temperature range of 390 to 480° C. through continuous vapor phase condensation in a flow reactor and distilling the resultant. The mixture is dehydrohalogenated in the presence of alkali metal hydroxide and a phase transition catalyst to form 3,4-difluorotoluene (IV). The 3,4-difluorotoluene is reacted with chlorine gas in the presence of catalysts consisting of ferro-shaving and ferric chloride at temperature range of −10 to 40° C. without using any organic solvent to form 2-chloro-4,5-difluorotoluene (V). The 2-chloro-4,5-difluorotoluene is photo-reacted with chlorine gas under a lighting mercury lamp at temperature range of 80 to 140° C. without using any organic solvent to form 2-chloro-4,5-difluorobenzotrichloride (VI). The 2-chloro-4,5-difluorobenzotrichloride is reacted with aqueous acid solution at temperature range of 35 to 80° C. without using any organic solvent to give 2-chloro-4,5-difluorobenzoic acid (VII). The 2-chloro-4,5-difluorobenzoyl chloride (VIII) according to the present invention is prepared by reacting 2-chloro-4,5-difluorobenzotrichloride (VI) with zinc oxide.

The distillate having low boiling point, which is obtained during distillation of the mixture of 4-chloro-1-methyl-4,5,5-trifluorocyclohexene (IIIa) and 5-chloro-1-methyl-4,4,5-trifluorocyclohexene (IIIb), may be recycled into the flow reactor.

The present invention may be better understood by reference to the following examples which are intended for purposes of illustration and are not to be confined in any way limiting the scope of the present invention, which is defined in the claims appended hereto.

EXAMPLES

Example 1

Preparations of 4-chloro-1-methyl-4,5,5-trifluorocyclohexene and 5-chloro-1-methyl-4,4,5-trifluorocyclohexene Example 1a A flow reactor equipped with dual tubes having 30 mm of inner diameter of the outer tube, 16 mm of outer diameter of the inner tube, and 1 m of length of the tubes was employed. The temperature in the reactor was kept at 440° C. Chlorotrifluoroethylene (CTFE) and isoprene were continuously injected into the flow reactor at the rate of 62.7 g/hr and 38.9 g/hr, respectively, and the vapor phase condensation was carried out for 44 hours. Then, unreacted chlorotrifluoroethylene (CTFE) of 0.42 kg was recovered. The resultant was purified by steam distillation and obtained as 3,100 Kg. The resultant was purified by fractional distillation under reduced pressure (70 mmHg) to give 1.77 kg of the desired cyclohexene mixture (IIIa/IIb-62/34) collected at temperature range of 84 to 88° C., as a colorless liquid. The distillate of 0.84 kg collected at temperature range of 46 to 83° C. was recycled for use in the vapor phase condensation in Example 1b.

Example 1b

Cyclohexene mixture was prepared in the same manner as in Example 1a except that the distillate collected at temperature range of 46 to 83° C. in Example 1a was recycled. The distillate was continuously injected to the flow reactor at the rate of 22.0 g/hr. The vapor phase condensation was carried out for 38 hours with chlorotrifluoroethylene (CTFE) and isoprene at the same rates as in Example 1a. Then, unreacted chlorotrifluoroethylene (CTFE) of 0.33 kg was recovered. The resultant was purified by steam distillation and the water layer was removed. The resultant of 3.58 kg was further purified by fractional distillation under reduced pressure (70 mmHg) to give 1.72 kg of the desired cyclohexene mixture (IIIa/IIb=62/34) collected at temperature range of 84 to 88° C., as a colorless liquid. And the distillate of 1.04 kg collected at temperature range of 46 to 83° C. was collected.

4- chloro-1-methyl-4,5,5-trifluorocyclohexene (IIIa):
$^1$H-NMR (CDCl$_3$) δ (ppm): 1.75(3H), 2.72(2H), 2.97 (2H), 5.28(1H)
$^{19}$F-NMR (CDCl$_3$) δ (ppm, CFCl$_3$): 110.5 & 112.7(2F., 246 Hz), 124.0(1F)

5-chloro-1-methyl-4,4,5-trifluorocyclohexene (IIIb):
$^1$H-NMR (CDCl$_3$) δ (ppm): 1.75 (3H), 2.76 (2H), 2.95 (2H), 5.31 (1H)
$^{19}$F-NMR (CDCl$_3$) δ (ppm, CFCl$_3$): 111.8 & 114.4 (2F. 246 Hz). 122.4(1F)

Examples 2–7 and Comparative Examples 1–3

4-chloro-1-methyl-4,5,5-trifluorocyclohexene and 5-chloro-1-methyl-4,4,5-trifluorocyclohexene were prepared in the same manner as in Example 1a except the reaction temperature and the injection rates of chlorotrifluoroethylene (CTFE) and isoprene, which are shown in Table 1. The contents of the cyclohexene mixture are shown in Table 1.

TABLE 1

| | reaction temperature (° C.) | injection rate of CTFE (g/hr) | injection rate of isoprene (g/hr) | Amount of the mixture after steam distillation (g/hr) | GC purity of (IIIa) + (IIIb) after steam distillation (%) |
|---|---|---|---|---|---|
| Examples | | | | | |
| 2 | 435 | 63.8 | 35.8 | 67.7 | 62 |
| 3 | 442 | 65.8 | 38.9 | 79.3 | 57 |
| 4 | 445 | 65.8 | 45.3 | 70.2 | 63 |
| 5 | 450 | 65.8 | 50.6 | 70.8 | 65 |
| 6 | 450 | 65.2 | 38.1 | 70.4 | 60 |
| 7 | 450 | 67.3 | 41.0 | 72.3 | 62 |
| Comparative Examples | | | | | |
| 1 | 500 | 65.2 | 38.1 | 54.1 | 54 |
| 2 | 520 | 51.2 | 30.0 | 34.8 | 44 |
| 3 | 520 | 65.2 | 38.1 | 45.2 | 52 |

Examples 8–11

Cyclohexene mixtures were prepared in the same manner as in Example 1b except reaction temperature, injection rates of chlorotrifluoroethylene (CTFE) and isoprene, and recycling distillate, which are shown in Table 2. The contents of the cyclohexene mixture are shown in Table 2.

TABLE 2

| Examples | Reaction temperature (° C.) | Injection rate of CTFE (g/hr) | Injection rate of isoprene (g/hr) | Injection rate of the recycling fraction (g/hr) | Amount of the mixture after steam distillation (g/hr) | GC purity of (IIIa) + (IIIb) after steam distillation (%) |
|---|---|---|---|---|---|---|
| 8 | 435 | 62.7 | 40.5 | 30.1 | 92.2 | 59 |
| 9 | 440 | 62.7 | 41.4 | 28.3 | 89.7 | 60 |
| 10 | 450 | 62.7 | 41.6 | 29.3 | 90.5 | 61 |
| 11 | 450 | 62.7 | 39.5 | 19.9 | 84.2 | 62 |

Example 12

Preparation of 4-chloro-3- methyl-4,5,5-trifluorocyclohexene

A flow reactor equipped with dual tubes having 30 mm of inner diameter of the outer tube, 16 mm of outer diameter of the inner tube, and 1 m of length of the tubes was employed. The temperature in the reactor was kept at 450° C. Chlorotrifluoroethylene (CTFE) and isoprene were continuously injected into the flow reactor at the rate of 71.0 g/hr and 41.2 g/hr, respectively, and the vapor phase condensation was carried out for 1 hour. Then, unreacted chlorotrifluoroethylene (CTFE) of 9.6 g was recovered. The resultant was purified by steam distillation and obtained as 71.2 g of the mixture (GC%=58%).
Cis+Trans isomers
$^1$H-NMR (CDCl$_3$) δ (ppm): 1.31+1.34(3H), 2.83(2H), 3.15(1H), 5.44(1H), 5.57(1H)
$^{19}$F-NMR (CDCl$_3$) δ (ppm, CFCl$_3$): (110.4&116.6)+ (108.0&111.2) (2F,244 Hz), 132.4–134.2(1F)

Comparative Example 4

Preparation of 4-chloro-3-methyl-4,5,5-trifluorocyclohexene

A flow reactor equipped with dual tubes having 20 mm of inner diameter of the outer tube, 16 mm of outer diameter of the inner tube, and 60 cm of length of the tubes was employed. The temperature in the reactor was kept at 520° C. Chlorotrifluoroethylene (CTFE), 1,3-pentadiene and nitrogen gas were continuously injected into the flow reactor at the rates of 36.1 g/hr, 20.4 g/hr, and 0.4 mol/hr, respectively, and the vapor phase condensation was carried out for 1 hour. Then, 4.7 g of unreacted chlorotrifluoroethylene (CTFE) was recovered. The resultant was purified by steam distillation, and then the water layer was removed to give 32.1 g of the mixture (GC%=52%).

Example 13

Preparation of 4-chloro-4,5,5-trifluorocyclohexene 4-chloro-4,5,5-trifluorocyclohexene was prepared in the same manner as in Example 12 except that chlorotrifluoroethylene (CTFE) and 1,3-butadiene were continuously injected into the flow reactor at the rates of 65.2 g/hr and 30.3 g/hr, respectively. Then, 8.6 g of unreacted chlorotrifluoroethylene (CTFE) was recovered. The resultant was purified by steam distillation, and then the water layer was removed to give 64.9 g of the mixture (GC%=61%).
$^1$H NMR (CDCl$_3$) δ (ppm): 2.82 (2H), 3.18 (2H), 5.65 (2H)
$^{19}$F-NMR (CDCl$_3$) δ (ppm, CFCl$_3$): 113.4 (2F), 122.2 (1F)

Comparative Example 5

Preparation of 4-chloro-4,5,5-trifluorocyclohexene 4-chloro-4,5,5-trifluorocyclohexene was prepared in the same manner as in Comparative Example 4 except that chlorotrifluoroethylene (CTFE), 1,3-butadiene and nitrogen gas were continuously injected into the flow reactor in the rates of 33.8 g/hr, 15.7 g/hr, and 0.4 mol/hr, respectively. Then, 4.7 g of unreacted chlorotrifluoroethylene (CTFE) was recovered. The resultant was purified by steam distillation, and then the water layer was removed to give 29.4 g of the mixture (GC%=53%).

Example 14

Preparation of 5-chloro-1,2-dimethyl-4,4,5-trifluorocyclohexene 5-chloro-1,2-dimethyl-4,4,5-trifluorocyclohexene was prepared in the same manner as in Example 12 except that chlorotrifluoroethylene (CTFE) and 1,3-butadiene were continuously injected into the flow reactor at the rates of 65.2 g/hr and 46.0 g/hr, respectively. Then, 8.1 g of unreacted chlorotrifluoroethylene (CTFE) was recovered. The resultant was purified by steam distillation, and then the water layer was removed to give 68.4 g of the mixture (GC%=57%).

$^{19}$F-NMR (CDCl$_3$) δ (ppm, CFCl$_3$): 111.4&114.5 (2F, 245 Hz). 123.4 (1F)

Comparative Example 6

Preparation of 5-chloro-1,2-dimethyl-4,4,5-trifluorocyclohexene 5-chloro-1,2-dimethyl-4,4,5-trifluorocyclohexene was prepared in the same manner as in Comparative Example 4 except that chlorotrifluoroethylene (CTFE), 2,3-dimethyl-1,3-butadiene, and nitrogen gas were continuously injected into the flow reactor at the rates of 33.8 g/hr, 23.8 g/hr and 0.4 mol/hr, respectively. Then, 5.8 g of unreacted chlorotrifluoroethylene (CTFE) was recovered. The resultant was purified by steam distillation, and then the water layer was removed to give 29.8 g of the mixture (GC%=51%).

Example 15

Preparation of 3,4-difluorotoluene

To a stirred mixture of 4-chloro-1-methyl-4,5,5-trifluorocyclohexene and 5-chloro-1-methyl-4,4,5-trifluorocyclohexene (1.20 kg) prepared in Example 1 was added 42 g of benzyltriethylammonium chloride, and then the reaction mixture was heated to 85° C. followed by slowly adding 2.15 kg of 50% aqueous sodium hydroxide solution over 4.5 hours. The reaction mixture was stirred for an additional 1.5 hours at 90° C. and then the resultant was purified by steam distillation followed by separating the aqueous layer. The organic layer was dried with 32 g of calcium chloride, and then 0.64 kg of the desired product was collected by fractional distillation at temperature range of 112° C. as a colorless liquid.

$^1$H-NMR (CDCl$_3$) δ (ppm): 2.30 (3H, s), 6.8–7.1 (3H, m)
$^{19}$F-NMR (CDCl$_3$) δ (ppm, CFCl$_3$): 138.7 (1F), 143.0 (1F)

Examples 16–21

3,4-difluorotoluene was prepared in the same manner as in Example 15 except alkali metal hydroxide, phase transfer catalyst, and reaction temperature, which are shown in Table 3. The contents of 3,4-difluorotoluene are shown in Table 3.

TABLE 3

| Examples | Alkali metal hydroxide | Phase transfer catalyst | Reaction temperature (° C.) | GC purity after steam distillation (%) |
|---|---|---|---|---|
| 16 | 50% aq. KOH | 18-crown-6 | 85 | 80 |
| 17 | 50% aq. KOH | Bu$_4$NBr | 85 | 85 |
| 18 | KOH | Et$_3$BnNCl | 85 | 78 |
| 19 | 30% aq. KOH | Et$_3$BnNCl | 85 | 50 |
| 20 | 50% aq. KOH | Et$_3$BnNCl | 60 | 59 |
| 21 | 50% aq. KOH | Et$_3$BnNCl | 85 | 85 |

Example 22

Preparation of 2,3-difluorotoluene

To a stirred solution of 4-chloro-3-methyl-4,5,5-trifluorocyclohexene of 58.6 g prepared in Example 12 was added 2.5 g of benzyltriethylammonium chloride, and then the reaction mixture was heated to 80° C. followed by slowly adding 240 g of 50% aqueous sodium hydroxide solution for 1 hour. The reaction mixture was stirred for additional 3 hours at 80° C., and then the resultant was purified by steam distillation followed by separating the aqueous layer. The organic layer was dried with calcium chloride, and then 32.3 g of the desired product was collected by fractional distillation as a colorless liquid.

$^1$H-NMR (CDCl$_3$) δ (ppm) : 2.32 (3H, s), 6.98 (3H, m)
$^{19}$F-NMR (CDCl$_3$) δ (ppm, CFCl$_3$): 139.1 (1F), 142.6 (1F)

Example 23

Preparation of 1,2-difluorobenzene

To a stirred solution of 4-chloro-4,5,5-trifluorocyclohexene of 24 g prepared in Example 13 was added 1.2 g of benzyltriethylammonium chloride, and then the reaction mixture was heated to 80° C. followed by slowly adding 100 g of 50% aqueous sodium hydroxide solution for 30 min. The reaction mixture was stirred for additional 2 hours at 80° C., and then the resultant was purified by steam distillation followed by separating the aqueous layer. The organic layer was dried with calcium chloride, and then 12.8 g of the desired product was collected by fractional distillation at temperature of 93° C. as a colorless liquid.

$^1$H-NMR (CDCl$_3$) δ (ppm): 7.0–7.2 (4H, m)
$^{19}$F-NMR (CDCl$_3$) δ (ppm, CFCl$_3$): 137.5 (2F)

Example 24

Preparation of 4,5-difluoro-ortho-xylene

To a stirred solution of 5-chloro-1,2-dimethyl-4,4,5-trifluorocyclohexene of 12.6 g prepared in Example 14 was added 1.0 g of benzyltriethylammonium chloride, and then the reaction mixture was heated to 80° C. followed by slowly adding 40 g of 50% aqueous sodium hydroxide solution for 30 min. The reaction mixture was stirred for additional 2 hours at 80° C., and then the resultant was purified by steam distillation followed by separating the aqueous layer. The organic layer was dried with calcium chloride, and then 7.3 g of the desired product was collected by fractional distillation at temperature 150° C. as a colorless liquid.

$^{19}$F-NMR (CDCl$_3$) δ (ppm, CFCl$_3$) : 143.8 (2F)

Example 25

Preparation of 2-chloro-4,5-difluorotoluene

To 925 g of 3,4-difluorotoluene prepared in Example 15 were added 17 g of shaving steel and 2.5 g of ferric chloride, and then chlorine gas was injected at the rate of 10.0 l/hr for 19 hours, maintaining the temperature between 15° C. The reaction mixture was washed with 10%/ aqueous sodium sulfite and water. After drying with 32 g of calcium chloride, the resultant was purified by fractional distillation to give 980 g of the desired product as a colorless liquid, collecting at temperature of 156° C.

$^1$H-NMR (CDCl$_3$) δ (ppm): 2.31(3H, s), 7.02(1H, dd), 7.16(1H, dd)

$^{19}$F-NMR (CDCl$_3$) δ (ppm, CFCl$_3$): 139.1(1F), 139.9(1F)

Example 26

Preparation of 2-chloro-4,5-difluorobenzotrichloride

To 300 g of 2-chloro-4,5-difluorotoluene prepared in Example 25 was added a flow of chlorine gas at the rate of 4.5 l/hr for 8 hours at 100° C. under a lighting mercury lamp. The rate of chlorine gas was increased to 7.0 l/hr for 10 hours at the inside temperature of 110° C., and then 5.0 l/hr for another 12 hours followed by purging the excess chlorine with nitrogen to give 472 g of the desired product as a colorless liquid. If necessary, the ultra pure product was obtained by distillation under reduced pressure (10 mmHg), collecting at temperature of 100° C.

$^1$H-NMR (CDCl$_3$) δ (ppm): 7.40 (1H, dd), 8.09 (1H, dd)

$^{19}$F-NMR (CDCl$_3$) δ (ppm, CFCl$_3$) 131.6 (1F), 136.5 (1F)

Example 27

Preparation of 2-chloro-4,5-difluorobenzoic acid

To 610 g of 85% sulfuric acid was slowly added 150 g of the distilled 2-chloro-4,5-difluorobenzotrichloride prepared in Example 26 at room temperature for 2 hours, and then the reaction mixture was stirred for 4 hours. The reaction mixture was stirred at 75° C. for 1 hour, and then poured into an ice water. The resultant was filtered and then air-dried to give 107 g of the desired product as white solid (mp=103–105° C.).

$^1$H-NMR (CDCl$_3$) δ (ppm): 7.35 (1H, dd), 7.95 (1H, dd), 11.50 (1H)

$^{19}$F-NMR (CDCl$_3$) δ (ppm, CFCl$_3$): 126.4 (1F), 137.0 (1F)

Example 28

Preparation of 2-chloro-4,5-difluorobenzoyl chloride

To 152 g of 2-chloro-4,5-difluorobenzotrichloride prepared in Example 26 was added 58 g of zinc oxide, and then the reaction mixture was stirred for 3 hours at 100° C. The desired product of 95 g was obtained by distillation under reduced pressure (5 mmHg), collecting at temperature range of 67 to 69° C. as a colorless liquid.

$^1$H-NMR (CDCl$_3$) δ (ppm): 7.50 (1H, dd), 8.14 (1H, dd)

$^{19}$F-NMR (CDCl$_3$) δ (ppm, CFCl$_3$): 126.5 (1F), 137.0 (1F)

The present invention can be easily carried out by an ordinary skilled person in the art. Many modifications and changes may be deemed to be within the scope of the present invention as defined in the following claims.

What is claimed is:

1. A method of preparing ortho-difluorobenzene derivatives (IV) according to the following reaction, which comprises:
   (a) providing a mixture of cyclohexenes (IIIa and IIIb) by reacting chlorotrifluoroethylene (CTFE) (I) and 1,3-diene (II) in a flow reactor at temperature range of 390 to 480° C. under atmospheric pressure through continuous vapor phase condensation and distilling the resultant; and
   (b) dehydrohalogenating the mixture of cyclohexenes (IIIa and IIIb) with a phase transition catalyst in the presence of alkali metal hydroxide at temperature range of 40 to 150° C. without using any organic solvent:

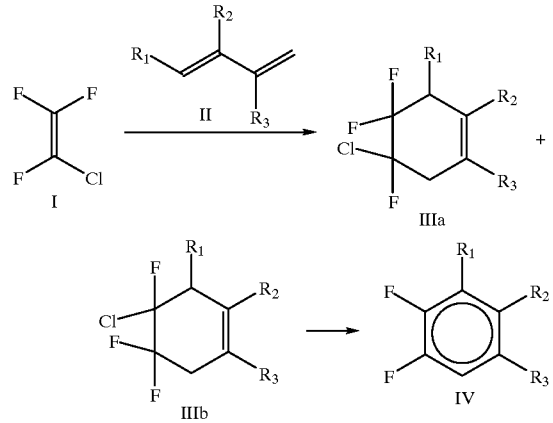

wherein R$_1$, R$_2$ and R$_3$ are independently a hydrogen atom or a lower alkyl group.

2. The method as defined in claim 1 wherein the molar ratio of said chlorotrifluoroethylene (CTFE) (I) to 1,3-diene (II) is in the range of 1.5:1 to 0.8:1, and the reaction time is in the range of 0.2 to 30 sec.

3. The method as defined in claim 1, wherein said reacting step of chlorotrifluoroethylene (I) and 1,3-diene (II) includes recycling the distillate having low boiling point, which is obtained during distillation of the resultant, into the flow reactor.

4. A method of preparing 2-chloro-4,5-difluorobenzoic acid (VII) according to the following reaction, which comprises:
   (a) providing a mixture of 4-chloro-1-methyl-4,5,5-trifluorocyclohexene (IIIa) and 5-chloro-1-methyl-4,4,5-trifluorocyclohexene (IIIb) by reacting chlorotrifluoroethylene (CTFE) (I) and isoprene (II) at temperature range of 390 to 480° C. through continuous vapor phase condensation in a flow reactor and distilling the resultant;
   (b) dehydrohalogenating said mixture in the presence of alkali metal hydroxide and a phase transition catalyst to form 3,4-difluorotoluene (IV);
   (c) reacting said 3,4-difluorotoluene with chlorine gas in the presence of catalysts consisting of ferro-shaving and ferric chloride at temperature range of –10 to 40° C. without using any organic solvent to form 2-chloro-4,5-difluorotoluene (V);
   (d) photo-reacting said 2-chloro-4,5-difluorotoluene with chlorine gas under a lighting mercury lamp at temperature range of 80 to 140° C. without using any organic solvent to form 2-chloro-4,5-difluorobenzotrichloride (VI); and (e) reacting said 2-chloro-4,5-difluorobenzotrichloride with aqueous acid solution at temperature range of 35 to 80° C. without using any organic solvent:

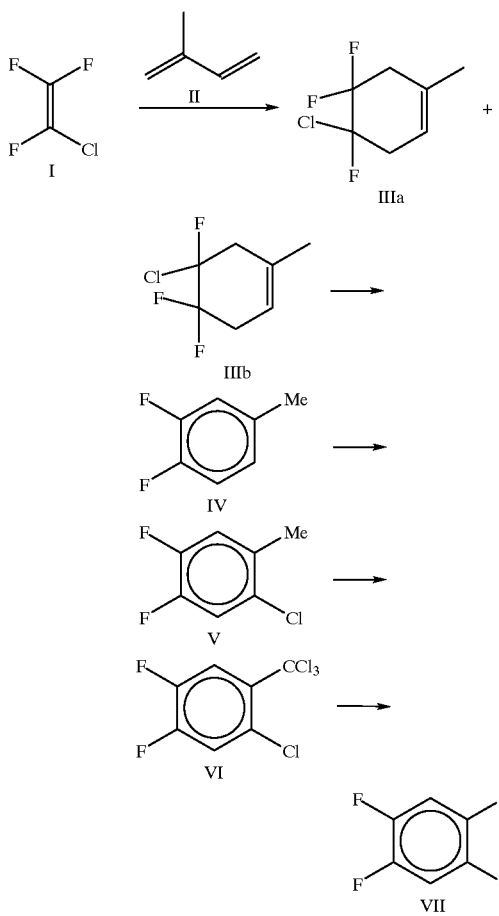

wherein Me represents a methyl group.

5. The method as defined in claim 4 wherein the molar ratio of said chlorotrifluoroethylene (CTFE) (I) to isoprene (II) is in the range of 1.5:1 to 0.8:1, and the reaction time is in the range of 0.2 to 30 sec.

6. The method as defined in claim 4, wherein said reacting step of chlorotrifluoroethylene (CTFE) (I) and isoprene (II) includes recycling the distillate having low boiling point, which is obtained during distillation of the resultant, into the flow reactor.

7. A method of preparing 2-chloro-4,5-difluorobenzoyl chloride (VIII) according to the following reaction, which comprises:
(a) providing a mixture of 4-chloro-1-methyl-4,5,5-trifluorocyclohexene (IIIa) and 5-chloro-1-methyl-4,4,5-trifluorocyclohexene (IIIb) by reacting chlorotrifluoroethylene (CTFE) (I) and isoprene (II ) at temperature range of 390 to 480° C. through continuous vapor phase condensation in a flow reactor and distilling the resultant;
(b) dehydrohalogenating said mixture in the presence of alkali metal hydroxide and a phase transition catalyst to form 3,4-difluorotoluene (IV);
(c) reacting said 3,4-difluorotoluene with chlorine gas in the presence of catalysts consisting of ferro-shaving and ferric chloride at temperature range of −10 to 40° C. without using any organic solvent to form 2-chloro-4,5-difluorotoluene (V);
(d) photo-reacting said 2-chloro-4,5-difluorotoluene with chlorine gas under a lighting mercury lamp at temperature range of 80 to 140° C. without using any organic solvent to form 2-chloro-4,5-difluorobenzotrichloride (VI;: and
(e) reacting said 2-chloro-4,5-difluorobenzotrichloride with zinc oxide:

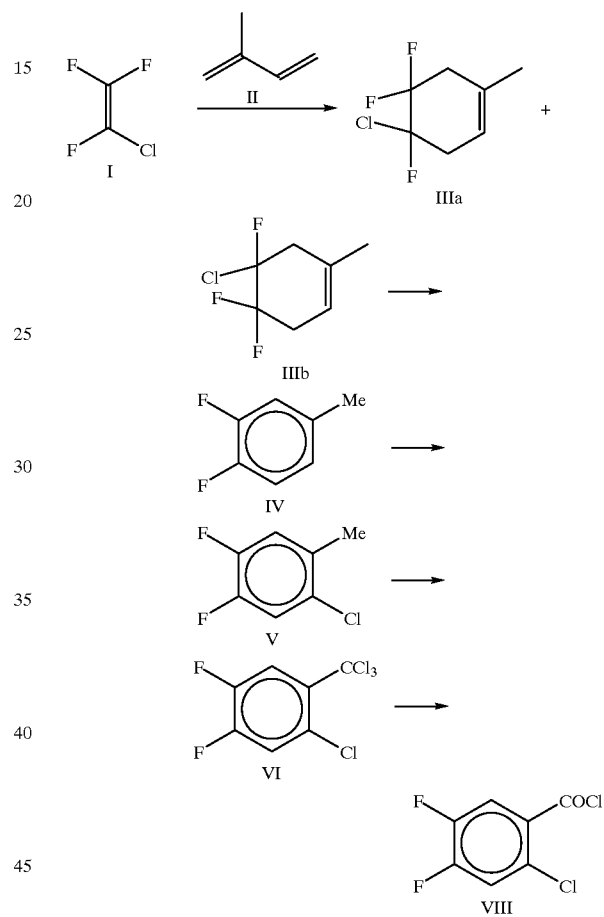

wherein Me represents a methyl group.

8. The method as defined in claim 7 wherein the molar ratio of said chlorotrifluoroethylene (CTFE) (I) to isoprene (II) is in the range of 1.5:1 to 0.8:1, and the reaction time is in the range of 0.2 to 30 sec.

9. The method as defined in claim 7, wherein said reacting step of chlorotrifluoroethylene (CTFE) (I) and isoprene (II) includes recycling the distillate having low boiling point, which is obtained during distillation of the resultant, into the flow reactor.

* * * * *

UNITED STATES PATENT AND TRADEMARK OFFICE
CERTIFICATE OF CORRECTION

PATENT NO. : 6,008,407
DATED : December 28, 1999
INVENTOR(S) : Nefedov et al.

It is certified that error appears in the above-identified patent and that said Letters Patent is hereby corrected as shown below:

On the Title Page:

Item [57]

In the Abstract at line 6, please delete ":he" and insert --the--

In the Abstract at line 18, please delete "to reacting" and insert --(c) reacting--

Signed and Sealed this

Twenty-seventh Day of March, 2001

Attest:

NICHOLAS P. GODICI

Attesting Officer

Acting Director of the United States Patent and Trademark Office